(12) United States Patent
Bae et al.

(10) Patent No.: US 8,158,080 B2
(45) Date of Patent: Apr. 17, 2012

(54) BIOSENSOR

(75) Inventors: Byeong-Woo Bae, Anyang (KR); Sung-Dong Lee, Anyang (KR); Byung-Hoon Kho, Seongnam (KR); Ji-Eon Ryu, Anyang (KR); Jin-Kyeong Kim, Gunpo (KR); Hyou-Arm Joung, Uiwang (KR); Ku-Cheol Ahn, Anyang (KR)

(73) Assignee: Infopia Co., Ltd. (KR)

( * ) Notice: Subject to any disclaimer, the term of this patent is extended or adjusted under 35 U.S.C. 154(b) by 41 days.

(21) Appl. No.: 12/722,226

(22) Filed: Mar. 11, 2010

(65) Prior Publication Data
US 2010/0311149 A1    Dec. 9, 2010

(30) Foreign Application Priority Data

Jun. 4, 2009  (KR) .................. 10-2009-0049646

(51) Int. Cl.
    *G01N 31/22*  (2006.01)
(52) U.S. Cl. ........................................ 422/428
(58) Field of Classification Search ............ 422/428
    See application file for complete search history.

(56) References Cited

U.S. PATENT DOCUMENTS

| | | |
|---|---|---|
| 5,597,532 A | 1/1997 | Connolly |
| 7,083,939 B2 | 8/2006 | Shull et al. |
| 7,087,397 B2 * | 8/2006 | Anaokar et al. ........ 435/11 |
| 7,214,504 B2 | 5/2007 | Anaokar et al. |
| 7,435,577 B2 | 10/2008 | Lawrence et al. |
| 7,494,818 B1 | 2/2009 | Anaokar et al. |

* cited by examiner

*Primary Examiner* — Bobby Ramdhanie
(74) *Attorney, Agent, or Firm* — Cantor Colburn LLP

(57) ABSTRACT

Disclosed herein is a biosensor. The biosensor includes a measuring layer configured to measure whether reaction to a biological sample has occurred. An upper cover is disposed on a top of the measuring layer, and is provided with an open window configured to allow a measurement area of the measuring layer to be exposed and an upper protrusion configured to protrude from an outer portion of the open window in a direction in which the upper protrusion is coupled to a lower panel. The lower panel is disposed below the measuring layer, and is provided with a lower protrusion which protrudes between the open window and the upper protrusion of the upper cover so that the lower protrusion is spaced apart from the upper protrusion by a gap and which presses the measuring layer so that a top of the measuring layer upwardly protrudes from the open window.

6 Claims, 8 Drawing Sheets

6-1    6-2    6-3    6-4

7-1
7-2

BIOSENSOR

BACKGROUND OF THE INVENTION

1. Field of the Invention

The present invention relates, in general, to biosensors, and, more particularly, to a vertical flow-type biosensor.

2. Description of the Related Art

The quantitative or qualitative analysis of analytic material present in a biological sample such as blood is important from a chemical or clinical standpoint. Representative examples thereof include the measurement of cholesterol which is the cause of various adult diseases and the measurement of blood sugar in blood for diabetics. As technology for measuring biological data such as cholesterol or blood sugar, methods of dropping a biological sample such as blood onto a measurement strip and detecting color change or electrochemical variation, which occurs as a result of enzymatic reaction in a reaction area, have been widely known.

In order to implement the above technology, technologies related to a measurement strip, that is, a biosensor, for measuring an analytic material contained in a biological sample have been proposed. For example, when blood sugar in blood is intended to be measured, a biosensor can measure the amount of blood sugar from extracted blood using an electrochemical method. However, the extraction of a biological sample including blood is an action that inflicts pain on the person whose biological sample is being extracted. As a result, in order to reduce pain, the amount of biological sample required for measurement needs to be minimized.

However, since the insufficiency of the amount of blood in a typical optical biosensor may greatly influence the results of analysis, it is important to load more than a predetermined amount of blood onto the measuring layer of the measurement strip. The volumes of red blood cells have a difference of 20 to 60% according to the human being. Accordingly, even if the same amount of blood is injected, there is the difference in the amount of blood serum which is separated from red blood cells and reaches a final reaction layer.

SUMMARY OF THE INVENTION

Accordingly, the present invention has been made keeping in mind the above problems occurring in the prior art, and an object of the present invention is to provide a biosensor which can minimize the difference in the amount of blood serum reaching a final reaction layer while minimizing the amount of biological sample required for measurement.

In order to accomplish the above object, the present invention provides a biosensor, comprising a measuring layer configured to measure whether reaction to a biological sample has occurred, an upper cover disposed on a top of the measuring layer, and provided with an open window configured to allow a measurement area of the measuring layer to be exposed and an upper protrusion configured to protrude from an outer portion of the open window in a direction in which the upper protrusion is coupled to a lower panel, and the lower panel disposed below the measuring layer, and provided with a lower protrusion which protrudes between the open window and the upper protrusion of the upper cover so that the lower protrusion is spaced apart from the upper protrusion by a predetermined gap and which presses the measuring layer so that a top of the measuring layer upwardly protrudes from the open window.

DESCRIPTION OF THE PREFERRED EMBODIMENTS

The above and other objects, features and advantages of the present invention will be more clearly understood from the following detailed description of preferred embodiments taken in conjunction with the accompanying drawings. Hereinafter, preferred embodiments of the present invention will be described in detail to allow those skilled in the art to easily understand and implement the present invention with reference to the attached drawings.

Figure 1:
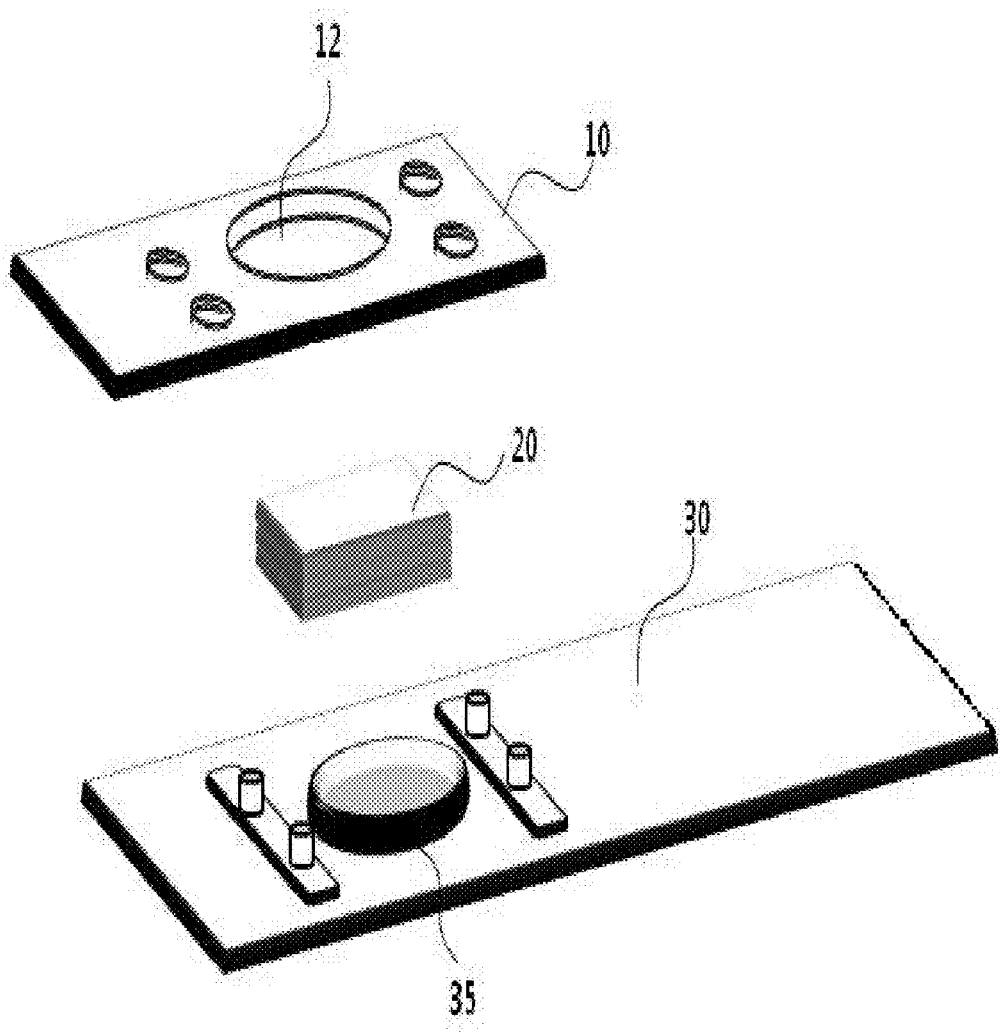
FIG. 1 is a diagram showing the construction of a biosensor according to an embodiment of the present invention.

FIG. 1 is a diagram showing the construction of a biosensor according to an embodiment of the present invention.

As shown in the drawing, the biosensor according to the embodiment includes a measuring layer 20, an upper cover 10 and a lower panel 30.

The measuring layer 20 is configured to measure whether reaction to a biological sample has occurred, and causes color change or electrochemical change while reacting to the biological sample.

The upper cover 10 includes an open window 12. In the present embodiment, the upper cover 10 includes an upper protrusion 15 which is spaced apart from the outer portion of the open window 12 by a predetermined distance and is configured to protrude towards the lower panel 30 and to downwardly press the measuring layer 20 disposed between the upper cover 10 and the lower panel 30.

The lower panel 30 includes a lower protrusion 35 which protrudes towards a region between the open window 12 and the upper protrusion 15 of the upper cover 10 to correspond to the edge of the open window 12. In the present embodiment, the lower protrusion 35 is configured to press the measuring layer 20 so that when the upper cover 10 and the lower panel 30 are coupled to each other, the top of the measuring layer 20 between the upper cover 10 and the lower panel 30 upwardly protrudes from the open window 12 of the upper cover 10 and the bottom of the measuring layer 20 is flattened. The size and length of the lower protrusion 35 are preferably determined according to the size of the open window 12 of the upper cover 10. The protrusion length of the lower protrusion 35 is caused to be uniform, thus enabling the bottom of the measuring layer to be pressed flat.

In an embodiment, the upper protrusion 15 of the upper cover 10 and the lower protrusion 35 of the lower panel 30 have different protrusion lengths. For example, the upper protrusion 15 may protrude at a length of 4 mm, and the lower protrusion 35 may protrude at a length of 3 mm. However, the protrusion lengths of the present invention are not limited to those examples.

In the present embodiment, since the upper protrusion 15 of the upper cover 10 and the lower protrusion 35 of the lower panel 30 are coupled to each other so that the lower protrusion 35 is spaced apart from the upper protrusion 15 by a predetermined gap, the top of the measuring layer 20 upwardly protrudes from the open window 12 of the upper cover 10 to be convex, and the bottom of the measuring layer is flattened.

Figure 2:
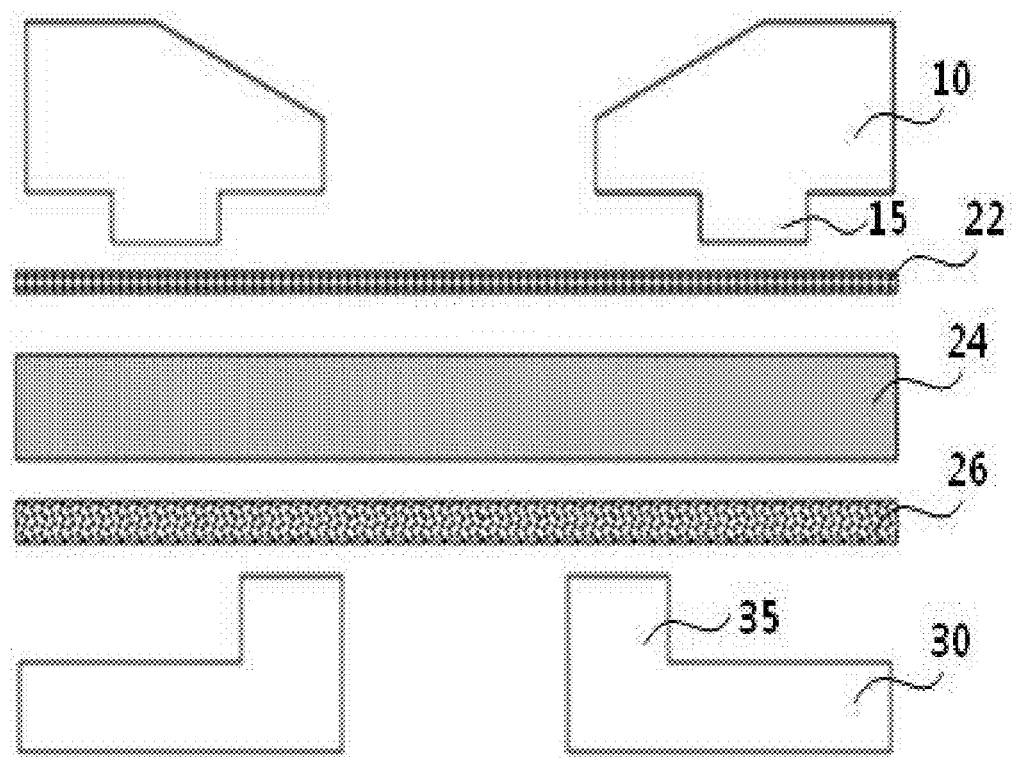
FIGS. 2 and 3 are diagrams showing in detail the measuring layer of the biosensor according to an embodiment of the present invention.
Figure 3:
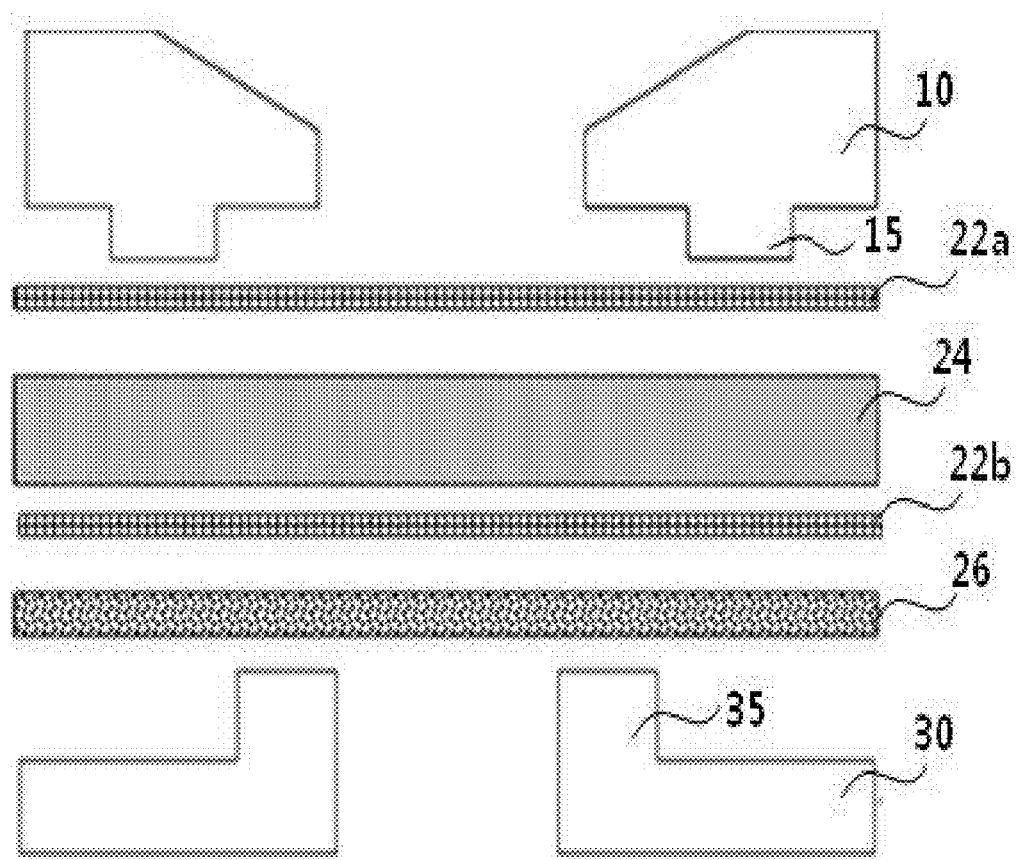

FIGS. 2 and 3 are diagrams showing in detail the measuring layer of the biosensor according to an embodiment of the present invention.

As shown in FIG. 2, the measuring layer according to the embodiment is implemented in a structure in which a spreading layer 22, a separating layer 24 and a reaction layer 26 are stacked on top of one another.

In detail, as shown in FIG. 3, the spreading layer 22 may include a first spreading layer 22a disposed on the top of the separating layer 24 and a second spreading layer 22b disposed on the bottom of the separating layer 24. That is, the spreading layer 22 may be implemented as at least one layer and may be provided between other layers.

The first spreading layer 22a allows the biological sample such as injected blood or plasma to be promptly and uniformly spread. In the present embodiment, the first spreading layer 22a may be made of, for example, woven material such as polyester or cotton, or non-woven fabric such as fabric, gauze or monofilament.

The separating layer 24 is placed below the first spreading layer 22a and is configured to separate blood cells such as red blood cells (also called erythrocytes) from the biological sample, that is, blood, spread by the first spreading layer 22a. In an embodiment, blood is separated into red blood cells and blood serum. The blood cells are formed as solid components such as red blood cells and white blood cells, and the blood serum is formed as a yellow-colored liquid. Red blood cells act as antigens (agglutinogens) and blood serum acts as an antibody (agglutinin). A vertical flow-type biosensor primarily separates red blood cells from the injected blood. Further, the results of reaction to the blood serum in a reaction area are observed, and thus the results of the analysis of analytic material can be checked.

In the present embodiment, the separating layer 24 can experimentally filter about 80 to 90% of the total red blood cells. In an embodiment, the separating layer 24 may be implemented in the form of a pad including a glass fiber. However, the separating layer 24 is not limited to those embodiments, and may be implemented in the form of a pad made of polyester, nitrocellulose or poly-sulfonate.

The second spreading layer 22b allows the biological sample from which part of red blood cells are separated by the separating layer 24 to be promptly and uniformly spread, thus enabling the biological sample to be promptly and uniformly absorbed into the reaction layer 26 placed below the second spreading layer 22b. In the present embodiment, the second spreading layer 22b may be implemented to have construction identical to or different from that of the first spreading layer 22a.

In an embodiment, the measuring layer 20 may further include a micro-separating layer disposed between the second spreading layer 22b and the reaction layer 26. The micro-separating layer is placed under the separating layer 24 and is configured to include in detail a glass microfiber, a cellulose fiber or a synthetic staple fiber in the present embodiment. In this case, the glass microfiber is implemented as a glass fiber having a diameter of 0.3 to 0.7 μm and a density of about 0.1 g/cm$^3$ or less. The micro-separating layer may separate the remaining red blood cells which the separating layer 14 failed to filter.

The reaction layer 26 is provided below the second spreading layer 22b or the micro-separating layer. In the present embodiment, the reaction layer 26 includes dry chemicals and reactant, and causes color change while reacting to cholesterol or the like.

In the present embodiment, the construction of the measuring layer is not limited to the above description, and may include various modifications. For example, it is possible that additional layers are further included between the existing layers so as to further improve the absorptivity of the biological sample or mutual propagation velocity between layers. In detail, a spreading layer may be disposed between layers to more promptly perform spreading.

Figure 4:
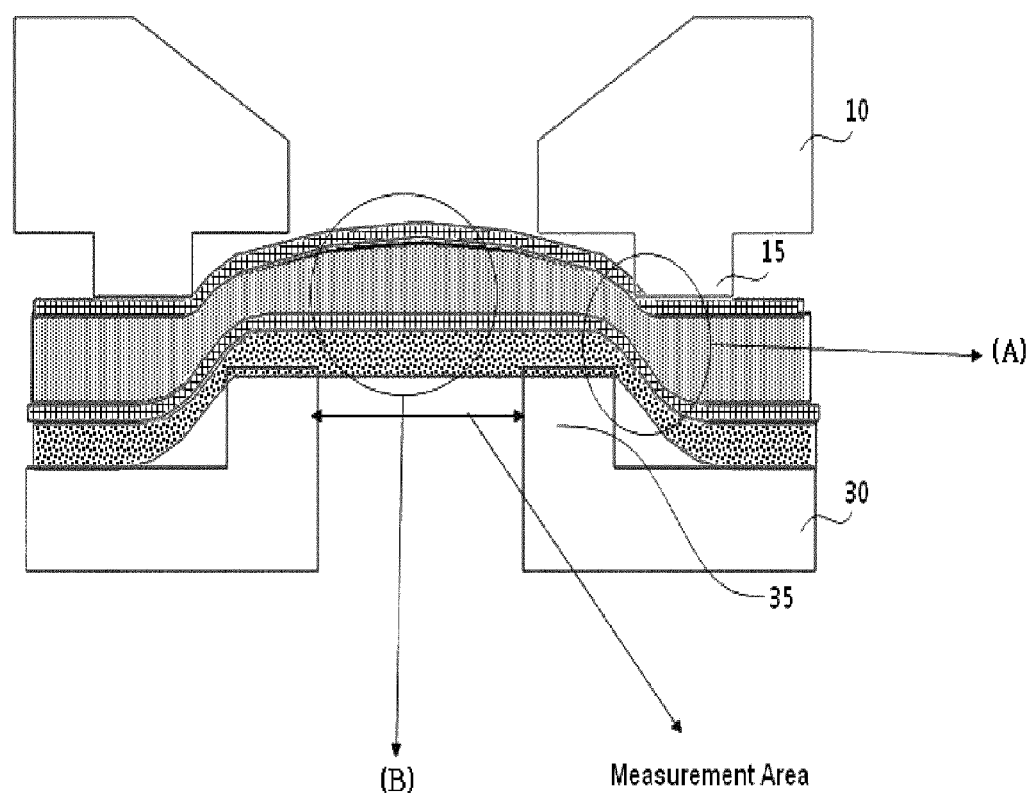
FIG. 4 is a diagram showing the construction of the biosensor in a coupled state according to an embodiment of the present invention.
Figure 5:
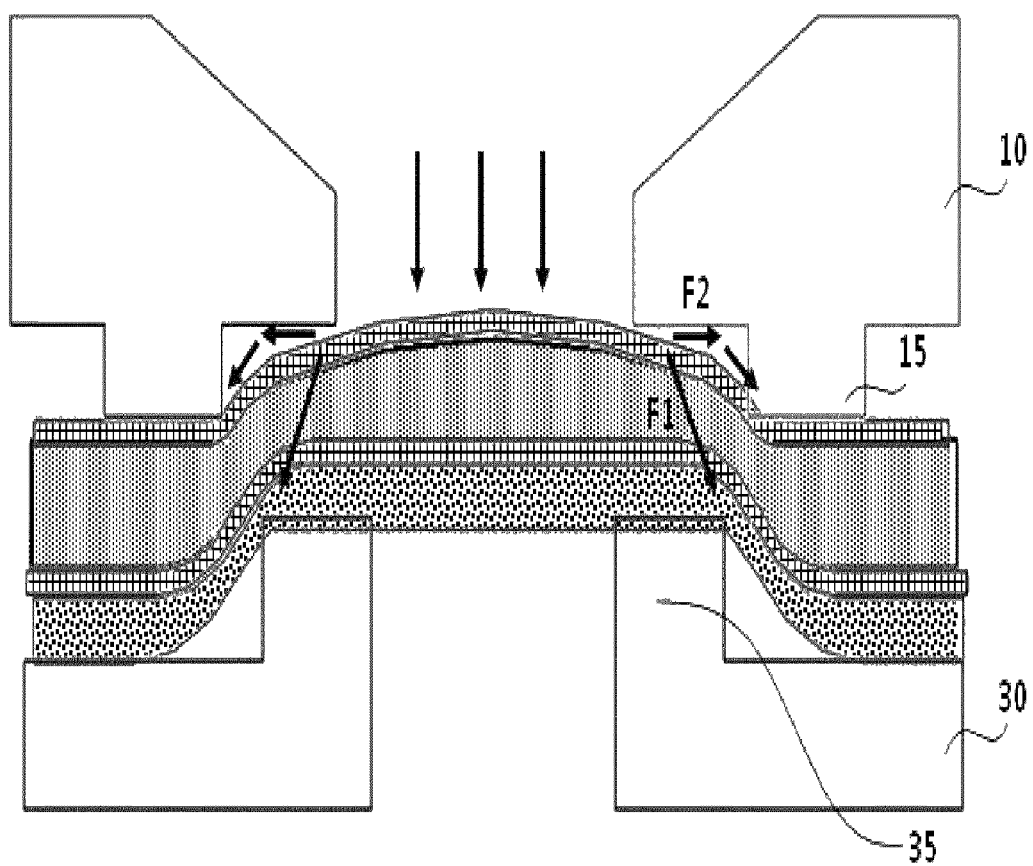
FIG. 5 is a diagram illustrating the flow of a biological sample injected into the biosensor sensor.

FIG. 4 is a diagram showing the construction of the biosensor in a coupled state according to an embodiment of the present invention, and FIG. 5 is a diagram illustrating the flow of a biological sample injected into the biosensor.

As shown in FIG. 4, since the measuring layer in which one or more layers are stacked on top of one another is pressed by the upper protrusion 15 and the lower protrusion 35 which are formed to be spaced apart from each other by a predetermined gap, the top of the measuring layer is upwardly convex, and the bottom of the measuring layer is flattened. In this way, since the measuring layer is pressed so that the top thereof is convex and the bottom is flat, the present invention can provide a structure in which the top is profitable for absorbing the biological sample such as blood and the bottom is profitable for ensuring the uniformity of the injected biological sample.

First, in the above structure, when a minimum of blood is injected through the open window of the upper cover, a relatively large amount of blood is loaded to the end portions of the open window because of the convex shape of the measuring layer. Further, as vertical flow gradually progresses, the blood is uniformly loaded into the reaction layer. When the flow of the blood is terminated in the reaction area of the reaction layer, the remaining amount of sample can no longer be injected into the reaction area, so that overflow is strengthened, and the remaining amount of sample flows to the outside of the reaction area.

Further, as shown in FIG. 5, at the end portions of the open window, the flow F1 of the sample which is absorbed into the lower portion of the measuring layer and the flow F2 of the sample which leaves the measuring layer coexist. Further, since the top of the measuring layer has a convex shape, vertical flow may occur on a larger scale, and thus loading speed may further increase near a measurement portion. At the point in time at which the flow of the biological sample progresses in the measurement area of the measuring layer and the biological sample is absorbed into all the surfaces of the measuring layer, the flow F1 of the biological sample towards the lower portion of the measuring layer does not occur any more, and only the flow F2 of the biological sample leaving the measuring layer is present. That is, as the amount of sample injected into the measurement area, only a certain amount of sample can be loaded regardless of the volume of red blood cells.

In an embodiment, even if the sample is loaded into only a measurement area having, for example, a diameter of about 3 mm, corresponding to the size of the open window rather than the entire size of the reaction layer of the biosensor, measurement can be performed. In the case of the biosensor of the present invention, even if a small amount of biological sample of about 4 μl to 10 μl is injected, an amount of sample sufficient to indicate a change in reaction in the measurement area of the reaction layer can be injected.

However, as described above, a great difference of 20 to 60% may occur in the volume of red blood cells contained in blood according to the human being. That is, even if the same amount of blood is injected, a difference may occur in the amount of blood serum which is separated from red blood cells and reaches the final reaction layer. Therefore, the amount of biological sample to be injected into the biosensor according to the embodiment of the present invention is preferably set based on a human being having a low serum/blood ratio. In the case of a human being having a high serum/blood ratio, there is a probability of causing an amount of sample, remaining after a predetermined amount of sample has been absorbed into the reaction layer, to overflow. Accordingly, the amount of biological sample to be injected into the biosensor is set based on a human being having a low serum/blood ratio, and thus the sample can be sufficiently injected into the reaction area.

As shown in FIG. 4, since the measuring layer 20 composed of a plurality of layers stacked on top of one another is pressed in a portion thereof in which the upper protrusion 15 and the lower protrusion 35 are coupled to be spaced apart from each other by a gap, the horizontal flow of blood injected into the open window 12 can be minimized.

In this case, the flow of the biological sample injected into a portion A in which the upper protrusion 15 and the lower protrusion 35 are coupled to be spaced apart from each other by a gap is formed in such a way that before the biological sample reaches the measuring layer 20, it flows in a downward vertical direction, and after the biological sample reaches the measuring layer 20, it spreads in a direction facing the inside or the outside of the measurement area in the measuring layer 20.

That is, in blood serum which is separated from red blood cells and reaches the measuring layer 20 by way of vertical flow, horizontal flow scarcely occurs in the measuring layer 20. In particular, since the measuring layer 20 is pressed in the portion A in which the upper protrusion and the lower protrusion are coupled to be spaced apart from each other by a gap, the horizontal flow of blood serum towards the inside of the reaction area is more easily conducted than the flow of blood serum towards the outside of the reaction area.

Further, since, by the coupling of the upper protrusion to the lower protrusion formed to be spaced apart from the lower protrusion by a gap, the measuring layer 20 is pressed such that the top thereof is upwardly convex and the bottom thereof, that is, the reaction layer 26, is flattened in the reaction area, that is, the center portion B of the open window, the uniformity of blood serum absorbed into the reaction layer 26 can be ensured.

Figure 6:
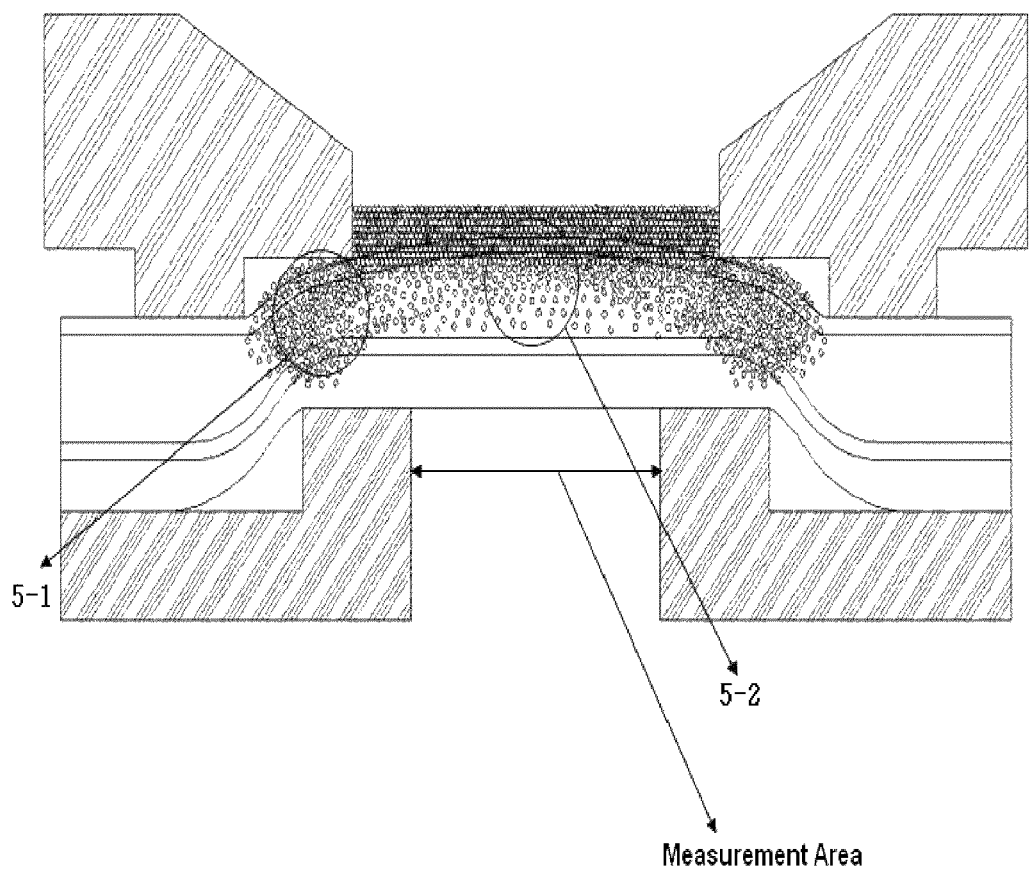
FIGS. 6 to 8 are diagrams illustrating the state of the injection of the biological sample over time.
Figure 7:
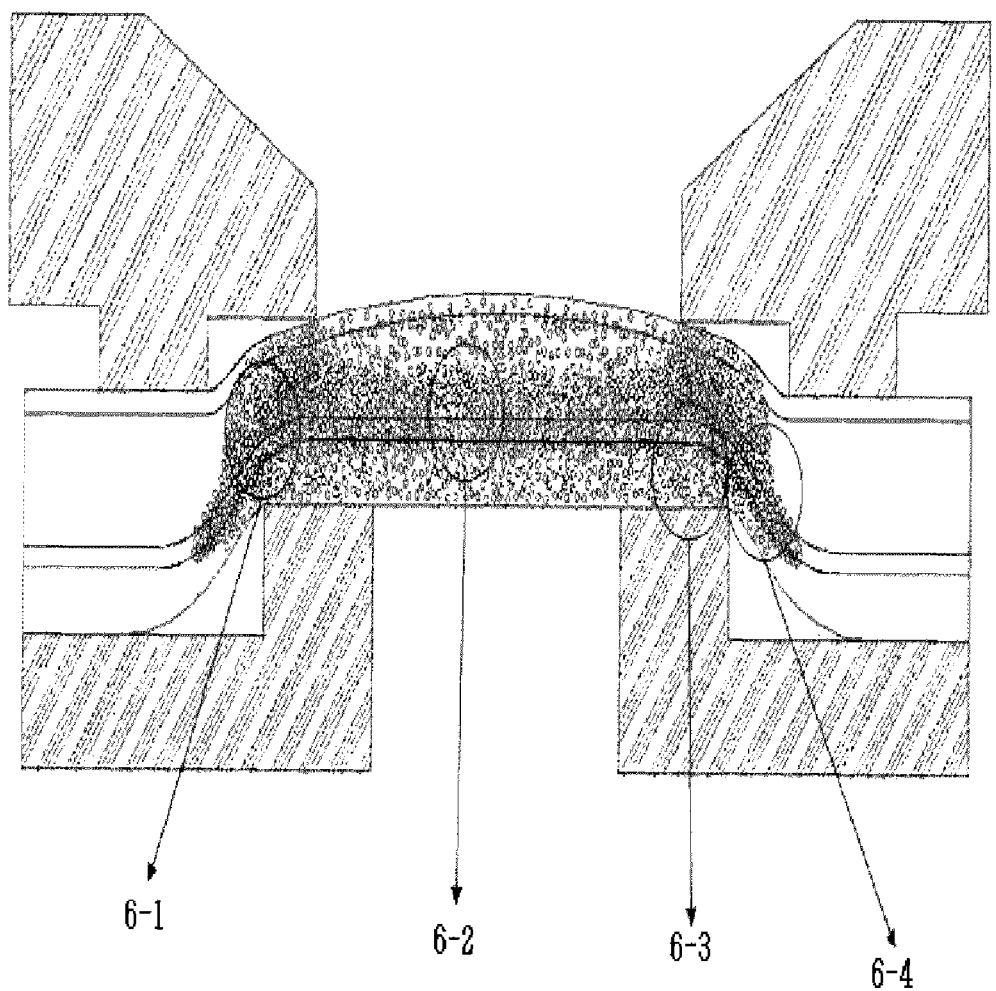
Figure 8:
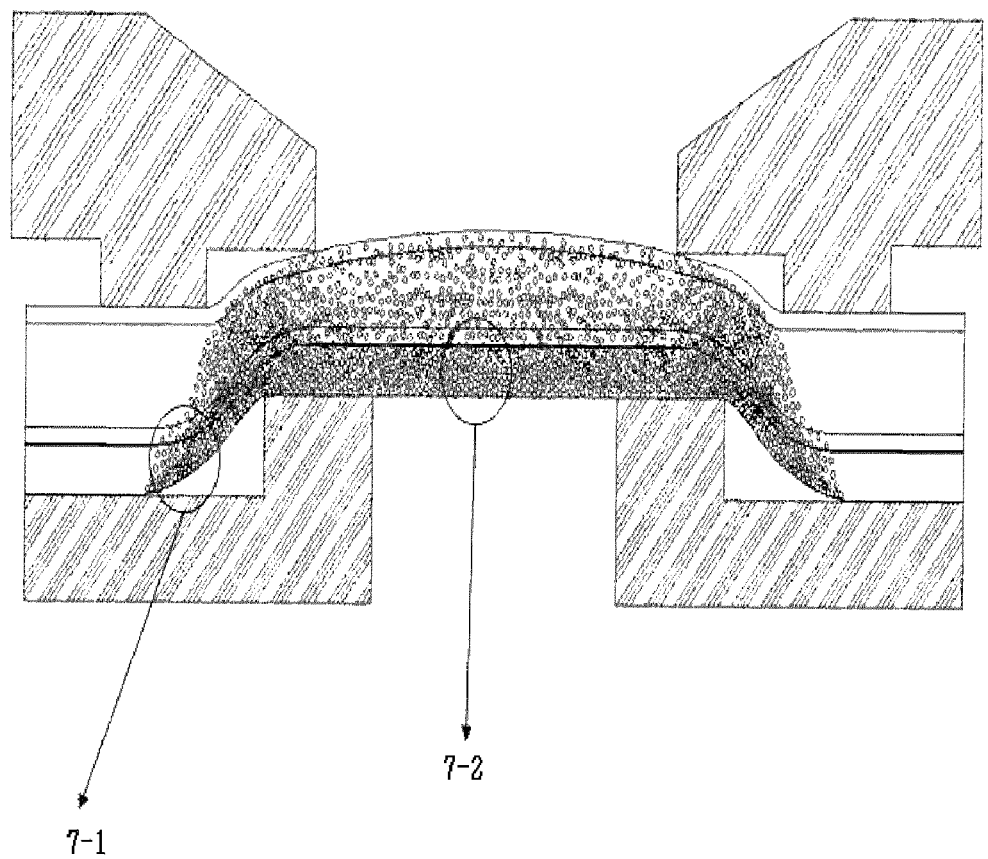

FIGS. 6 to 8 are diagrams illustrating the state of the injection of a biological sample over time.

First, in order to observe reaction occurring in the biosensor, a biological sample such as blood is dropped into the open window 12. At the initial stage of sample injection at which a long duration of time does not pass, the vertical flow of the sample appears strongly at the end portions 5-1 of the open window, that is, at the end portions of the measurement area, as shown in FIG. 6. In this case, since the measuring layer is pressed such that the center portion thereof is upwardly convex because of the upper protrusion of the upper cover and the lower protrusion of the lower panel, there is the effect of further increasing the speed of vertical flow at the end portions of the measurement area. In contrast, compared to the strong vertical flow at both end portions, a small amount of vertical flow occurs at the center portion 5-2 of the measurement area.

The biological sample that was absorbed into the end portions 6-1 of the open window 12 at the initial stage scarcely progresses in a horizontal direction. In this state, when a predetermined duration of time passes, the biological sample reaches the measuring layer 20 according to the vertical flow at the end portions of the open window, and thereafter horizontally moves so that it spreads in a direction facing the center and the outside of the open window 12, as shown in FIG. 7. In this case, due to the structure of the measuring layer, the progress of the biological sample towards the center portion of the measurement area rather than towards the outside of the measurement area is more strongly conducted.

Here, the vertical flow of the sample at the center portion 6-2 of the open window continuously occurs. Therefore, the sample at the center portion also reaches the reaction layer placed in a lowermost portion of the measuring layer according to the vertical flow of the sample.

Meanwhile, a largest amount of sample reaches the area 6-3 of the measuring layer in the gap by which the upper protrusion is spaced apart from the lower protrusion. Therefore, horizontal flow occurs first in the reaction layer placed in the lowermost portion of the measuring layer. Further, part of the sample flows to a direction 6-4 facing the outside of the measurement area.

As shown in FIG. 8, when a long duration of time passes, a sample which progresses from both end portions to the center portion of the measurement area and a sample which reaches the reaction layer in the lowermost portion according to the vertical flow are saturated, and thus the horizontal flow towards the center portion of the measurement area stops in the reaction layer.

When the flow of the sample towards the center portion of the measurement area stops in the reaction layer, the horizontal flow to the outside of the reaction layer increases, and the remaining amount of sample gradually moves to the outside 7-1 of the measurement area. Accordingly, the amount of sample accumulated (7-2) in the reaction layer of the measurement area can be maintained at a uniform amount. Furthermore, in an embodiment of the measurement area other than the entire reaction layer, even if a biological sample is loaded into only a region having a diameter of 3 mm, measurement can be performed. Therefore, the biosensor capable of measuring reaction using only a biological sample such as a small amount of blood of about 4 µl to 10 µl can be provided.

According to the present invention, a biosensor enabling the amount of biological sample required for measurement to be minimized can be provided.

Further, the present invention can provide a biosensor which corrects measurement errors attributable to the volume of red blood cells by minimizing the difference in the amount of blood serum reaching a reaction area, thus more accurately indicating the results of reaction.

Although the preferred embodiments of the present invention have been disclosed for illustrative purposes, those skilled in the art will appreciate that various modifications, additions and substitutions are possible, without departing from the scope and spirit of the invention as disclosed in the accompanying claims. Therefore, the above embodiments should be considered from a descriptive standpoint rather than a restrictive standpoint. The scope of the present invention is disclosed in the accompanying claims, and all differences belonging to equivalent scope thereof should be interpreted as being included in the present invention.

What is claimed is:

1. A biosensor, comprising:
  a measuring layer configured to measure whether reaction to a biological sample has occurred;
  an upper cover disposed on a top of the measuring layer, and provided with an open window having a first width configured to allow a measurement area of the measuring layer to be exposed and an upper protrusion configured to be spaced apart from an outer portion of the open window by a predetermined distance and configured to protrude in a direction in which the upper protrusion is coupled to a lower panel; and
  the lower panel disposed below the measuring layer, and provided with a lower protrusion configured to protrude between the open window and the upper protrusion of the upper cover to form the measurement area having a second width, the second width being smaller than the first width, wherein the lower protrusion is spaced apart from the upper protrusion by a predetermined gap and is configured to press the measuring layer so that a top of the measuring layer upwardly protrudes from the open window.

2. The biosensor according to claim 1, wherein the lower protrusion presses the measuring layer so that a bottom of the measuring layer is flattened.

3. The biosensor according to claim 1, wherein the measuring layer changes color thereof according to a reaction to the biological sample.

4. The biosensor according to claim 1, wherein the measuring layer comprises:
 a spreading layer for spreading an injected biological sample;
 a separating layer for separating the biological sample spread by the spreading layer into blood serum and red blood cells; and
 a reaction layer coated with chromophoric reagent causing color change according to reaction to the blood serum separated from the red blood cells by the separating layer.

5. The biosensor according to claim 4, wherein the spreading layer comprises:
 a first spreading layer disposed on a top of the separating layer; and
 a second spreading layer disposed on a bottom of the separating layer.

6. The biosensor according to claim 4, wherein the separating layer comprises at least one of glass fiber, polyester, nitrocellulose, and poly-sulfonate.

* * * * *